United States Patent [19]
Rollins et al.

[11] Patent Number: 5,179,078
[45] Date of Patent: Jan. 12, 1993

[54] METHOD OF SUPPRESSING TUMOR FORMATION IN VIVO

[75] Inventors: Barrett Rollins, Brookline; Charles Stiles, Newton Center, both of Mass.

[73] Assignee: Dana Farber Cancer Institute, Boston, Mass.

[21] Appl. No.: 701,515

[22] Filed: May 16, 1991

Related U.S. Application Data

[63] Continuation-in-part of Ser. No. 351,008, May 12, 1989.

[51] Int. Cl.⁵ ............... C12N 1/20; A01N 37/18; A61K 37/00; C07K 5/00
[52] U.S. Cl. .................................. 514/2; 514/12; 435/252.3; 530/324; 530/351
[58] Field of Search ............ 435/252.3; 530/324, 530/351; 514/2, 12

[56] References Cited

PUBLICATIONS

Graves et al. (Sep. 1989) *Science* vol. 245, pp. 1490–1493.
Valente et al. '(1988) *Biochemistry* vol. 27, pp. 4162–4168.

*Primary Examiner*—David L. Lacey
*Assistant Examiner*—Gian P. Wang
*Attorney, Agent, or Firm*—Hamilton, Brook, Smith & Reynolds

[57] ABSTRACT

A method of suppressing tumor formation in a vertebrate by administering JE/MCP-1 is described. Also described are methods of treating localized complications of malignancies and methods of combatting parasitic infection by administering JE/MCP-1.

6 Claims, 4 Drawing Sheets

METHOD OF SUPPRESSING TUMOR FORMATION IN VIVO

GOVERNMENT SUPPORT

The invention described herein was supported in whole or in part by grants from the National Institute of Health.

RELATED APPLICATION

This application is a Continuation-In-Part of U.S. patent application Ser. No. 07/351,008 filed May 12, 1989, the contents of which are incorporated herein by reference.

BACKGROUND

Cancer results when a vertebrate's own cells become malignant. Healthy individuals at any given time carry potentially malignant cells in their body. These cells are generally recognized and killed by the individuals' immune system. However, some malignant cells are not destroyed by the immune system and proliferate into tumors.

Currently, there are not adequate and specific therapies for cancer. For example, surgical excision of tumors is not an effective method of treatment where the cancer has metastasized. In addition, radiation and chemotherapy often kill normal cells in addition to cancerous cells.

Another problem is that chemotherapeutic agents follow first-order kinetics. As a result, a constant percentage, rather than a constant number of cells are killed by a given application of a chemotherapeutic agent. Consequently, malignant cells, which could cause a relapse in the disease, remain even when a patent is diagnosed as having complete clinical remission.

A method of suppressing cancer that employs the individual's own immune system would be useful.

SUMMARY OF THE INVENTION

The present invention relates to Applicant's finding that expression of the JE/Monocyte Chemoattractant Protein-1 (JE/MCP-1) malignant cells suppresses their ability to form tumors in vivo. Thus, the invention comprises, in one embodiment, a method of suppressing tumor formation in a vertebrae by administering to the vertebrate a therapeutically effective amount of JE/MCP-1. The protein can be administered alone or as an adjuvant to surgery or cytotoxic chemotherapy.

The suppressive effect of JE/MCP-1 depends on the induction of the vertebrate's immune response, specifically the response of monocytes. Thus, in another embodiment, the invention comprises a method of increasing a vertebrate's monocyte-mediated tumoricidal activity in vivo by administering to the vertebrate an effective amount of JE/MCP-1.

JE/MCP-1 can also be administered to treat localized complications of malignancy. For example, JE/MCP-1 could be used to inhibit malignant pleural effusions or ascites. Therefore, in a further embodiment, the invention comprises methods of inhibiting pleural effusion or ascites in a vertebrate by locally administering JE/MCP-1 to the anatomic spaces between the lung and the plural membrane or the stomach and the peritoneum.

In a further embodiment tumor killing cells, such as tumor infiltrating lymphocytes (TIL cells) are genetically engineered to express the JE/MCP-1 protein. The engineered cells therefore can be administered to a vertebrate to provide a synergistic local tumor cell killing.

The presence of JE/MCP-1 in vivo is accompanied by an local increase in the presence of eosinophils. Therefore, another aspect of the subject invention comprises methods of combatting a parasitic infection in a vertebrate animal by administering to that vertebrate an effective amount of JE/MCP-1.

A major advantage of using JE/MCP-1 in treating cancer is that it employs the individual's own immune system and therefore would have fewer side-effects than conventional chemotherapies. In addition, JE/MCP-1 stimulates monocytes and, as such, does not depend on a total immunologic response.

BRIEF DESCRIPTION OF THE DRAWINGS

FIG. 2A CHO cells only, $10^7$ OA-2 cells (open square); $10^7$ OA-2 cells plus $10^7$ hJEC-10 cells (closed square and closed circle); $10^7$ OA-2 cells and $10^7$ 10A-10 cells (closed triangle and open triangle); (identical results were obtained with $10^7$ OA-2 cells and $10^7$ hJEC-100 cells). FIG. 2B. CHO and HeLa cells. $10^5$ HeLa cells and $10^7$ OA-2 cells (open square and open circle); $10^5$ HeLa cells and $10^7$ hJEC-10 cells (closed square and closed circle); $10^5$ HeLa cells and $10^7$ 10A-10 cells (closed triangle and open triangle); (identical results were obtained with $10^7$ HeLa cells and $10^7$ hJEC-100 cells in 3 out of 4 animals).

DETAILED DESCRIPTION OF THE INVENTION

Figure 1:
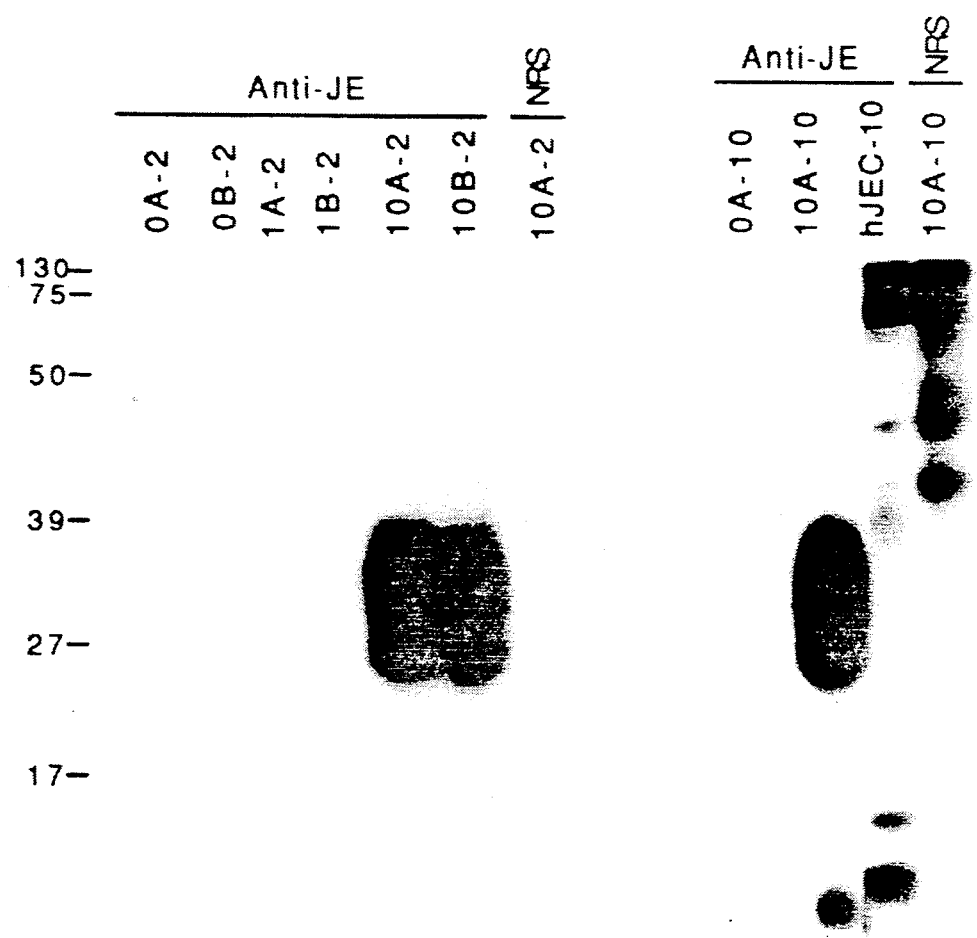
FIG. 1 is an autoradiograph of polyacrylamide gel electrophoresis of cells of DUKX-B11 cells transfected with pXM alone (OA-2, OB-2, and OA-10), pXM-JE1 (1A-2 and 1B-2), pXM-JE10(10A-2, and 10B-2, and 10A-10), or pXM-hJE34 (hJEC-10 and hJEC-100).

The present invention is based on the finding that expression of the JE/MCP-1 protein in malignant cells suppresses their ability to form tumors in vivo.

The JE gene is a platelet-derived growth factor (PDGF)-inducible "competence" or "early response gene" first identified in mouse 3T3 cells (Cochran, B. H. Cell 33:939–947 (1983)). Sequence and expression analysis showed that unlike other early response genes, such as c-myc, c-fos, or c-jun, the murine JE gene encodes a secreted glycoprotein with cytokine-like properties (Kawahara, R. S. *J. Biol. Chem.* 264:679–682 (1989); Rollins, B. J. *Proc. Natl. Acad. Sci. USA* 85:3738–3742 (1988)). The human homolog of murine JE has been cloned, (Rollins, B. J. *Mol. Cell. Biol.* 9:4687–4695 (1989)), and the predicted amino acid sequence of its protein is identical to that of a monocyte chemoattractant, MCP-1 (Yoshimura, T., *J. Exp. Med.* 169:1449–1459 (1989) (Yoshimura T. *JE FEBS Lett.* 244:487–493 (1989)) also called MCAF (Furutani, Y. et al., *Biochem. Biophys. Res. Commun.* 159:249–255 (1989); Matsushima, K. et al., *J. Exp. Med.*

169:1485-1490 (1989) and SMC-CF (Graves, D. T. et al., *Science* 245:1490-1493 (1989); Valente, A. J. et al. *Biochem* 27;4162-4168 (1988)).

The JE/MCP-1 protein is structurally related to the members of a large, recently identified family of low molecular weight secreted proteins that appear to be involved in the inflammatory response (Leonard, E. J. and T. Yoshimura *Immunol. Today* 11:97-101 (1990); Rollins, B. J. et al., *Mol. Cell. Biol.* 9:4687-4695 (1989); Wolpe, S. D. and A. Cerami, *FASEB J.* 3:2563-2573 (1989)). The genes for many of these proteins, including human JE/MCP-1, are clustered on chromosome 17q11.2-12 (Donlon, T. A. et al., *Genomics* 6:548-553 (1990); Irving, S. G., et al., *Nucleic Acids Res.* 18:3261-3270 (1990); Rollins, B. J., et al., *Genomics* (in press)) or mouse chromosome 11 (Wilson, S. D., et al., *J. Exp. Med.* 171:1301-1314 (1990)). These genes are also elated to the genes encoding another family of cytokines, whose members include the neutrophil activator NAP-1/IL-8 (Peveri, P., et al., *J. Exp. Med.* 167:1547-1559 (1988); Schroder, J. M. et al. *J. Immunol* 139:3474-3483 (1987); Yoshimura, T. et al., *Proc. Natl. Acad. Sci. USA* 84:9233-9237 (1987)), many of which cluster at 4q12-21 (Griffin, C. A. et al., *Cytogenet Cell Genet* 45:67-69 (1987); Luster, A. D. et al. *Proc. Natl. Acad. Sci. USA* 84:2868-2871 (1987); Richmond, A. *EMBO J.* 7:2025-2033 (1988)).

JE/MCP-1 exerts several effects specifically on monocytes. Both natural and recombinant JE/MCP-1 are potent chemoattractants for human monocytes in vitro, (Matsushima, K. et al. *J. Exp. Med.* 169:1485-1490 (1989); Yoshimura, T. et al. *J. Exp. Med.* 169:1449-1459 (1989)) and purified recombinant JE/MCP-1 can stimulate an increase in cytoslic free calcium and the respiratory burst in monocytes (Zachariae, C. O. C., et al., *J. Exp. Med.* 171:2177-2182 (1990); Rollins, B. J. et al. *Blood* (in press)). Purified natural JE/MCP-1 has also been reported to activate monocyte-mediated inhibition of tumor cell growth, but not tumor cell killing, in vitro (Matsushima, K. et al. *J. Exp. Med.* 169:1485-1490 (1989)).

The following demonstrates that expression of the JE gene in malignant cells suppresses their ability to form tumors in vivo. This apparent phenotypic reversion requires interaction with host factors in vivo, since expression of JE/MCP-1 does not alter the transformed character of these cells in vitro. Furthermore, the following shows that JE/MCP-1-expression cells exert their effect in trans by their ability to suppress tumor formation when co-injected with JE/MCP-1-non-expressing tumor cells.

In order to create malignant cells expressing JE/MCP-1, the DHFR deletion mutant CHO cell line, DUKXB-11 (G. Urlaub and L. A. Chasin, *Proc. Natl. Acad. Sci. USA*, 77:4216-4220 (1980)) was transfected with the expression vector pXM (Yang, Y. C. et al. *Cell* 47:3-10 (1986) containing a variety of JE cDNA species. High levels of JE/MCP-1 protein expression were achieved in stably transfected lines by methotrexate (MTX-induced DNA amplification. R. J. Kaufman, et al., *EMBO J.* 6:187-193 (1987).

FIG. 1 shows JE/MCP-1 protein expression in independently derived cell lines selected for resistance to 2 or 10 uM MXT. There is no detectable JE/MCP-1 protein secreted from cell lines transfected with pXM alone (cell lines OA-2 and OB-2; cell line OA-10 was derived from OA-2) or with pXM containing murine JE cDNA in the antisense orientation (1A-2 and 1B-2). Considerable JE/MCP-1 protein was secreted by cell lines transfected with murine JE cDNA in the sense orientation (10A-2 and 10B-2; 10A-10 was derived from 10A-2) and human JE cDNA (hJEC-10). Cell line hJEC-100, derived from hJEC-10 by selecting for resistance to 100 um MTX, also secreted human JE/MCP-1 protein.

Murine JE cDNA directs CHO cells to secrete a microheterogenous protein of $M_r$ 27–39,000, similar to the natural protein and the protein expressed in a COS cell expression system. Rollins, B. J. et al., *Proc. Natl. Acad. Sci. USA* 85:3738:3742 (1988)). Nearly half of the apparent $M_r$ is due to O-linked glycosylation. Human JE/MCP-1 proteins expressed in CHO cells are also similar to native and COS cell expressed JE/MCP-1 α ($M_r$15,000) and JE/MCP-1β ($M_r$11,000). (Rollins, B. J., et al. *Mol. Cell. Biol.* 9:4687-4695 (1989)).

The monocyte chemoattractant activities (MCA) secreted by these cell lines were determined as described in detail in Example 1. They were 1415 U/24hr/$10^6$ cells (10A-2), 1079 U/24hr/$10^6$ cells (10B-2), U/24hr/$10^6$ cells (10A-10), 54 U/24hr/$10^6$ cells (hJEC-10), and 692 U/24hr/$10^6$ cells (hJEC-100) JE/MCP-1-non-expressing cells secreted 10–30 U/24hr/$10^6$ cells. The increased MCA secreted by murine JE/MCP-1 expressing lines is due to increased JE/MCP-1 protein in the medium, not to higher specific activity. Murine JE/MCP-1 appears to be more stable than human JE/MCP-1 in culture, perhaps due to its more extensive glycosylation. (Rollins, B. J., et al. *Mol. Cell. Biol.* 9:4687-4695 (1989)).

By several criteria, JE/MCP-1 expression did not alter the transformed phenotype of CHO cells in vitro. Table I shows that while doubling times of each of the independently derived cell lines varied considerably, the average doubling time of all the JE/MCP-1-expressing lines (25.1 hrs±5.7 sd) was nearly identical to the average doubling time of the JE/MCP-1-non-expressers (26.4 hrs±5.7 sd). Also, JE/MCP-1 expression did not alter the transformed cellular morphology of the CHO cells. Finally, all cell lines formed colonies in soft agar.

TABLE 1

PROPERTIES OF TRANSFECTED CHINESE HAMSTER OVARY CELL LINES.

| Cell Line | JE cDNA | Doubling Time (hours) | Soft Agar Colonies/25 mm$^2$ | No. Cells Injected | Tumors/Animal Injected |
|---|---|---|---|---|---|
| JE/MCP-1 Non-expressors ||||||
| OA-2 | None | 24.2 | 91 ± 14.0 | 2 × $10^7$ | 1/1 |
| " | " | " | " | 1 × $10^7$ | 2/2 |
| " | " | " | " | 2 × $10^6$ | 3/4 |
| OA-10 | None | 20.4 | 32 ± 1.9 | 1 × $10^7$ | 2/2 |
| OB-2 | None | 19.0 | 73 ± 2.6 | 1 × $10^7$ | 0/4 |
| 1A-2 | Antisense | 30.7 | 75 ± 14.5 | 8 × $10^6$ | 2/2 |
| 1B-2 | Antisense | 31.2 | 74 ± 1.7 | 1 × $10^7$ | 1/2 |

TABLE 1-continued

PROPERTIES OF TRANSFECTED CHINESE HAMSTER OVARY CELL LINES.

| Cell Line | JE cDNA | Doubling Time (hours) | Soft Agar Colonies/25 mm$^2$ | No. Cells Injected | Tumors/Animal Injected |
|---|---|---|---|---|---|
| JE/MCP-1 Expressors | | | | | |
| 10A-2 | Murine | 28.8 | 72 ± 7.3 | 2 × 10$^7$ | 0/1 |
| " | " | " | " | 1 × 10$^7$ | 0/2 |
| " | " | " | " | 2 × 10$^6$ | 0/4 |
| 10B-2 | Murine | 17.8 | 86 ± 5.1 | 1 × 10$^7$ | 0/2 |
| 10A-10 | Murine | 30.0 | 129 ± 6.8 | 1 × 10$^7$ | 0/2 |
| hJEC-10 | Human | 28.8 | 32 ± 6.8 | 1 × 10$^7$ | 0/2 |

In vivo, however, JE/MCP-1 expression led to a striking difference in behavior. Table 1 shows that all but one (OB-2) of the JE/MCP-1-non-expressing cell lines formed large subcutaneous tumors that appeared within three weeks of injection into nude mice. In contrast, all of the JE/MCP-1-expressing lines, including the human JE/MCP-1 expressing lines, formed no tumors for as long as ten months after injection. At autopsy, there was no microscopic evidence of residual tumor in the animals that received JE/MCP-1-expressing cells.

These observations suggested the possibility that JE/MCP-1-secreting cells attracted monocytes to the site of tumor cell injection and once there, secreted JE/MCP-1 protein induced monocyte tumoricidal activity. To test this hypothesis, JE/MCP-1-expressing cells were mixed with 10$^7$ OA-2 cells, a number of cells that reproducibly led to tumor formation when injected alone (see Table 1).

Figure 2A:
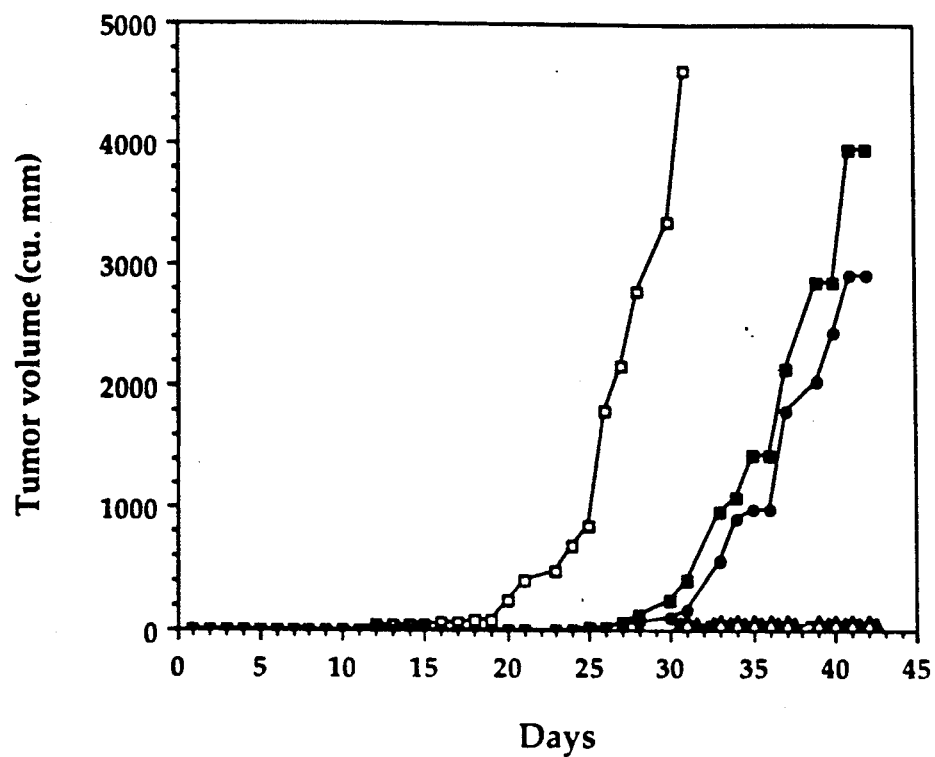
FIGS. 2A and 2B are graphs plotting the growth rate of tumors. Each symbol represents a different mouse.

FIG. 2A shows that co-injection of murine JE/MCP-1-expressing cells (10A-10) with OA-2 cells completely suppressed tumor formation in two animals. Co-injection of high-level human JE/MCP-1-expressing cells (hJEC-100) with OA-2 cells also completely suppressed tumor formation. Co-injection of low-level human JE/MCP-1-expressing cells (hJEC-10) suppressed tumor formation for 8-10 days, after which tumors appeared. Presumably hJEC-10 cells exerted a suppressive effect transiently until the proliferating OA-2 cell mass reached a size that enabled it to escape the effect.

Figure 2B:
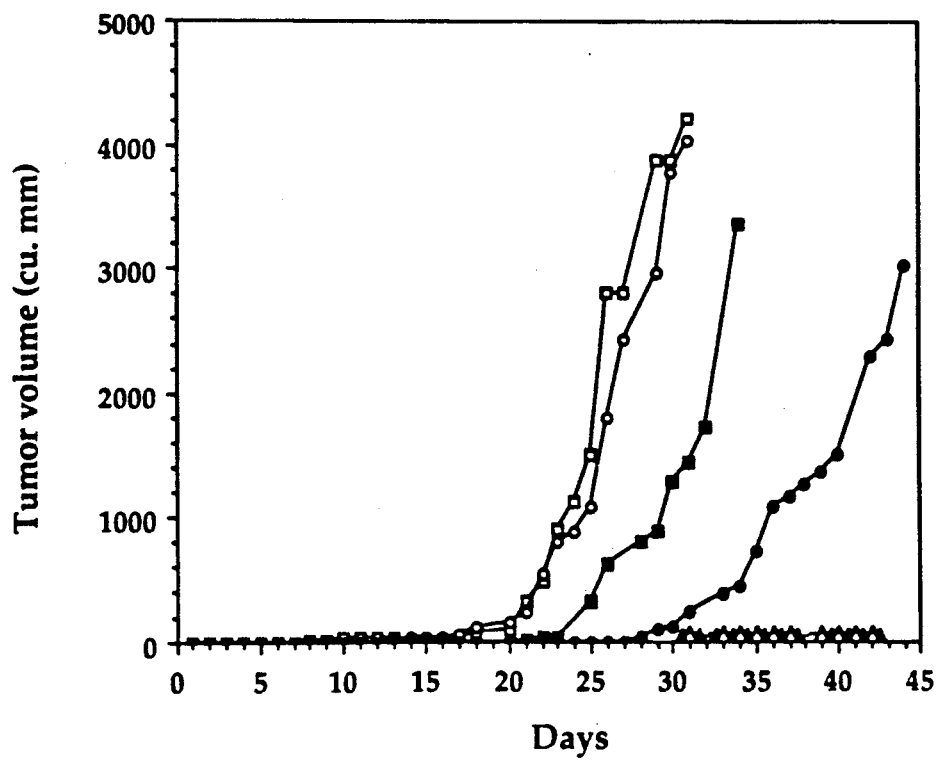

JE/MCP-1-expressors and non-expressors were also co-injected with HeLa cells to test whether JE/MCP-1-expression could suppress tumor formation by another cell type. FIG. 2B shows that 10A-10 cells completely suppressed the formation of tumors by HeLa cells. As above, co-injection with hJEC-10 cells delayed tumor formation. In a separate experiment, 4 of 4 animals injected with 10$^7$ HeLa cells formed tumors, while only 1 of 4 animals injected with 10$^7$ HeLa cells plus 10$^7$ hJEC-100 cells formed tumors. Mice that displayed no tumor growth after receiving HeLa plus hJEC-100 cells were then injected with 10$^7$ HeLa cells alone. These mice developed large tumors within 14 days, indicating that prior suppression of HeLa cell tumor growth in the presence of JE/MCP-1 does not render mice immune to rechallenge with HeLa cells.

Histolgoic examination of the tumors arising from co-injected HeLa and OA-2 cells revealed a mixture of epithelioid HeLa cells and spindle-shaped CHO cells. Examination of the tumors formed in animals that received HeLa and hJEC-10 cells also demonstrated a mixture of HeLa cells and CHO cells. The presence of some hJEC-10 cells in these tumors was confirmed by Northern blot analysis in which expression of human JE mRNA could be detected. After reaching a certain size, these tumors may overwhelm the host response elicited by the low levels of human JE/MCP-1 secreted by hJEC-10 cells. However, tumor growth still requires the presence of a malignant JE/MCP-1-non-expressing cell line, since hJEC-10 cells injected by themselves cannot form tumors (Table 1). This suggests again that the intrinsic growth properties of the CHO cells have not been altered by JE/MCP-1 expression, and that the human JE/MCP-1 expressors will proliferate in vivo if they are protected by an enlarging mass of malignant cells.

Figure 3A:
FIGS. 3A, 3B and 3C are photographs (magnification 400X) of hematoxylin and eosin-stained cellular infiltrate elicited by FIG. 3A. OA-10, FIG. 3B. 10A-10 or FIG. 3C. hJEC-10 cells.
Figure 3B:
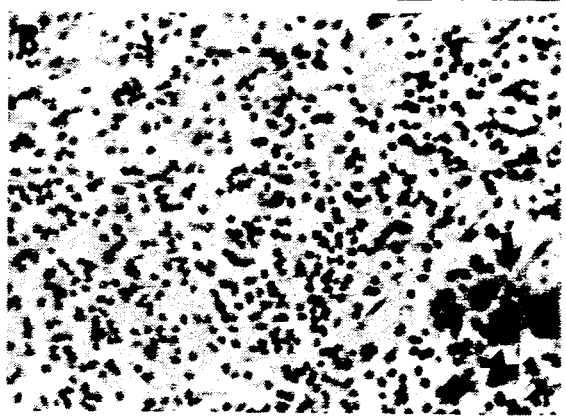
Figure 3C:
Figure 4A:
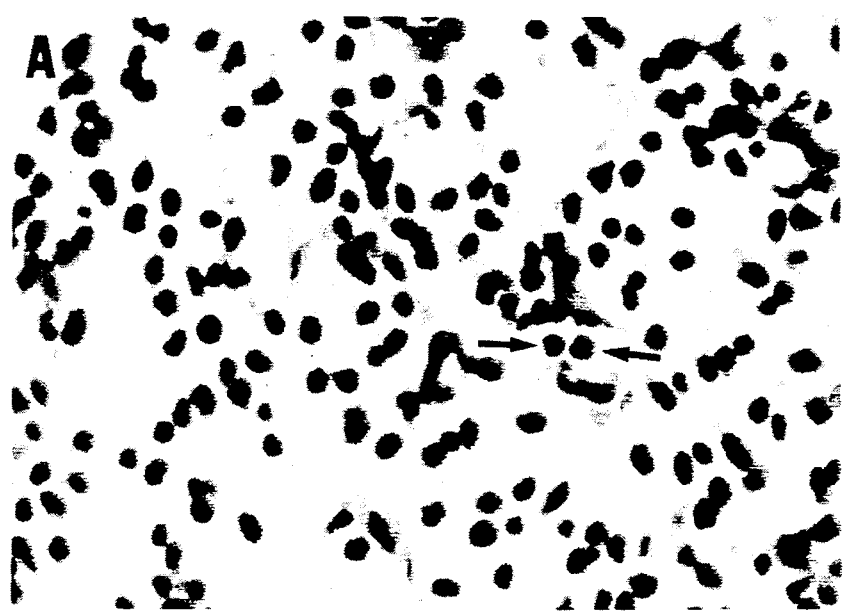
FIGS. 4A and 4B are photographs (magnification 400X) of hematoxylin and eosin-stained cellular infiltrate elicited by hJEC-10 cells.
Figure 4B:

FIGS. 3 and 4 show the results of a histological examination of the sites of CHO cell inoculation 24 hours after cells were injected. JE/MCP-1-non-expressors (darkly stained, large cells indicated by arrows in FIG. 3A) induce the appearance in the underlying connective tissue of only a few cells, most of which are neutrophils. In contrast, CHO cells expressing murine JE/MCP-1 (indicated by arrows in FIG. 3B) elicited an abundant cellular infiltrate. At higher power (FIG. 4A), it is apparent that this infiltrate consisted primarily of monocytes with a reproducibly significant proportion of eosinophils (arrows), usually 10-20%. As might be expected, low-level human JE/MCP-1-expressing cells (hJEC-10) induced a qualitatively similar infiltrate (FIG. 4B) that was intermediate in intensity between the non-expressors and the murine JE/MCP-1 expressors (compare FIG. 3C to FIGS. 3A and 3B).

The results represented by FIG. 3 and 4 demonstrate a predominantly monocytic infiltrate at the site of tumor cell injection, suggesting that monocytes mediate tumor growth suppression. The effect is probably not mediated by T lymphocytes or by natural killer cells, since purified recombinant JE/MCP-1 has no stimulatory effect on natural killer cells in vitro.

If monocytes are responsible for tumor suppression, there are several possible mechanisms whereby JE/MCP-1-activated monocytes might exert their effects. JE/MCP-1 could induce the expression of a soluble mediator of tumor cells lysis such as tumor necrosis factor (TNF). L. J. Old, Science, 230: 630–632 (1985). J. L. Urban et al., Proc. Natl. Acad. Sci. USA 83: 5233–5237 (1986). Alternatively, TNF could be expressed and displayed in an active form on the cell surface of activated monocytes. M. Kriegler, et al., Cell 53: 45–52 (1988).

Interestingly, an eosinophilic component to the inflammatory cell infiltrate was also observed. This may be either a direct effect of JE/MCP-1 or, JE/MCP-1 may induce the expression of another factor with eosinophil chemoattractant properties.

These results point to a clinical role for infused JE/MCP-1 in vertebrate animals, such as humans. For example, JE/MCP-1 can be administered to patients with cancer. This would necessarily be limited to patients with low tumor loads, i.e. as an adjuvant to surgery or cytotoxic chemotherapy. Systemically infused JE/MCP-1 would lead to a generalized increase in the activation state of a vertebrate's monocytes. There is some evidence that patients harboring malignancies have depressed monocyte function. W. G. Chaney et al., *Cell Molec. Genet*, 5: 15–27 (1986). E. S. Kleinerman et al., *Lancet ii:* 1102–1105, (1980). If the defect were cytokine based, rather than an inherent monocyte defect, JE/MCP-1 infusion would correct the abnormality.

Alternatively, JE/MCP-1 may prove useful in treating localized compositions of malignancy, such as pleural effusions or ascites. Instilling JE/MCP-1 into the involved anatomic space (e.g. the space between the lung and the pleural membrane or the space between the stomach and the peritoneum) can lead to local monocyte accumulation and activation.

As a therapeutic, JE/MCP-1 can be administered to vertebrate animals, (i.e. animals having an immune system), including humans. The compounds of this invention can be employed in admixture with conventional excipients, i.e., pharmaceutically acceptable organic or inorganic carrier substances suitable for parental or topical application.

Suitable pharmaceutical carriers include, but are not limited to water, salt solutions, alcohols, polyethylene glycols, gelatin, carbohydrates such as lactose, amylose or starch, magnesium stearate, talc, silicic acid, viscous paraffin, perfume oil, fatty acid esters, hydroxymethylcellulose, polyvinyl pyrrolidone, etc. The pharmaceutical preparations can be sterilized and if desired, mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds. They can also be combined where desired with other active agents, e.g., enzyme inhibitors, to further reduce metabolic degradation.

For parenteral application, particularly suitable are injectable, sterile solutions, preferably oily or aqueous solutions, as well as suspensions, emulsions, or implants, including suppositories. Ampoules are convenient unit dosages.

For topical application, there are employed as nonsprayable forms, viscous to semi-solid or solid forms comprising a carrier compatible with topical application and having a dynamic viscosity preferably greater than water. Suitable formulations include but are not limited to solutions, suspensions, emulsions, creams, ointments, powders, liniments, salves, aerosols, etc., which are, if desired, sterilized or mixed with auxiliary agents, (e.g., preservatives, stabilizers, wetting agents, buffers of salt for influencing osmotic pressure, etc.). For topical application, also suitable are sprayable aerosol preparations wherein the active ingredient, preferably in combination with a solid or liquid inert carrier material, is packaged in a squeeze bottle or in admixture with a pressurized volatile, normally gaseous propellant, e.g., a Freon.

It will be appreciated that the actual preferred amounts of JE/MCP-1 in a specific case will vary according to the specific compound being utilized, the particular compositions formulated, the mode of application, and the particular situs and organism being treated. Dosages for a given host can be determined using conventional considerations, (e.g., by means of an appropriate, conventional pharmacological protocol.).

Alternatively, tumor killing cells, such as tumor infiltrating lymphocytes (TIL cells) could be genetically engineered to express the JE/MCP-1 protein. Tumor killing cells engineered in this way can provide synergistic local tumor cell killing. The tumor killing cells could be engineered in vitro and administered to the vertebrate or the tumor killing cells could be engineered in vivo into the vertebrate's own supply of tumor killing cells using methods which are known in the art.

The present invention will now be illustrated by the following examples, which are not intended to be limiting in any way.

EXAMPLE 1

In Vivo Tumoricidal Effect of JE/MCP-1

Cell culture. DUKXB-11 cells (Urlaub, G. and L. A. Chasin, *Proc. Natl. Acad. Sci. USA*, 83:5233–5237 (1987)) (dihydrofolate reductase (DHFR) mutant Chinese hamster ovary (CHO) cells) were grown in the alpha modification of minimal essential medium (MEM-α) without ribonucleosides and deoxyribonucleosdes, supplemented with 10% bovine calf serum and 10 ug/ml adenosine, deoxyadenosine, and thymidine (MEM-α/BCS/ATT). (Kaufman, R. J. et. al. *EMBO J.* 6: 187–193, (1989)). HeLa cells were grown in Dulbecco's modified Eagle's medium (DMEM) supplemented with 10% heat-inactivated calf serum and antibiotics.

*Transfections and Methotrexate (MTX)* selection DUKXB-11 cells were grown in 10 cm culture dishes as described above. At 60% confluence, medium was removed and replaced with fresh MEM-α/BCS/AAT supplemented with 3 ug/ml polybrene and incubated overnight. (Chaney, W. G. et al., *Somat. Cell Molec. Genet.*, 12:237–244, (1986)). The next day, each dish was given 3 ml fresh MEM-α/MCS/AAT with 83 ng/ml plasmid DNA and 10 ug/ml polybrene. Cells were incubated at 37° C. for 6 hr with rocking every 90 min. Medium was then removed and replaced with 5 ml fresh MEM-α/BCS/AAT containing 30% DMSO for exactly 4 min. Medium was removed, the cells were washed once with MEM-α, and given 10 ml of MEM-α/BCS/AA. Cells were incubated at 37° C. for 48 hr, then trypsinized and re-plated into 4 culture dishes (10 cm) in nucleoside- and deoxynuycleoside-free MEM-α supplemented with 10% dialyzed BCS, and refed with this medium every 3 days. Two independent transfections were performed using pXM (Yang et al. *Cell* 47:3–10 (1986); pXM-JE10 (murine JE cDNA (Rollins, B. J., et al., *Proc. Natl. Acad. Sci. USA* 85:3738–3742 (1988)) in the sense orientation), pXM-JE1 (murine JE cDNA in the antisense orientation), and pXM-hJE34 (human JE cDNA) Rollins, B. J., et al., *Mol. Cell. Biol.* 9:4687–4695 (1989)). Colonies from each independent transfection that grew in ribonucleoside- and deoxyribonucleoside-free medium were trypsinized and combined. Step-wise selection in increasing concentrations of methotrexate (MTX) was carried out at the following levels: 0.02 uM, 0.1 uM, 0.5 uM, 2.0 uM, 10.0 uM, and 100.0 uM. At each concentration, surviving colonies were trypsinized and pooled.

Protein analysis. Confluent cell cultures were incubated in methionine-free MEM-α with 2% dialyzed BCS for 45 min, then changed to 0.5 ml of the same medium with 500 uCi [$^{35}$S]methionine (DuPont NEN, Boston, Mass.). Cells were incubated at 37° C. for 4 hrs. after which the medium was collected, made 1 mM in phenylmethylsulfonyl fluoride (PMSF), centrifuged to remove cells and debris, and stored at −70° C. Immune precipitations using anti-JE/MCP-1 antiserum were performed (Rollins, B. J., et al., *Mol. Cell. Biol.* 9:4687-4695 (1989)) and the results analyzed by electrophoresis through an SDS-containing 17% polyacrylamide gel.

Soft agar colony formation assay. Five thousand cells were suspended in MEM-α containing 10% dialyzed BCS, 0.3% agar, and the appropriate concentration of MTX. While still molten, this suspension was distributed on a gelled 4 ml underlayer of MEM-α containing 10% dialyzed BCS, 0.6% agar, and the appropriate concentration of MTX in a 60 mm culture dish. Cells were fed with 3 drops of fresh medium every 5 days. After 14 days, colonies consisting of greater than 50 cells were counted.

Monocyte chemoattractant activity (MCA). Confluent monolayers of CHO cells were incubated in serum-free MEM-α for 24 hr, after which the medium was centrifuged to remove cells and debris, and the remaining adherent cells were trypsinized and counted. Fresh human peripheral blood mononuclear cells were purified from the blood of volunteer donors by centrifugation on a cushion of Ficoll-Hypaque (Pharmacia, Piscataway, N.J.). Cells at the interface were washed twice in Gey's balanced salt solution (GBSS) with 2% BSA, then resuspended at $4 \times 10^6$ cells/ml in GBSS with 0.2% BSA, and MCA was measured in a 48-well microchamber apparatus. (Falk, W., et al., *J. Immunol. Methods* 33:239-247 (1980)). The concentration of MCA in CHO cell medium was defined as the reciprocal of the dilution showing half-maximal activity. (Yoshimura, T., et al., *J. Exp. Med.* 169:1449-1459 (1989)).

Nude mouse injections. Cells were suspended in 0.2 ml PBS and injected subcutaneously into 4-week old mass Swiss nu/nu mice. Mice were monitored daily for tumor growth. Tumor volume was derived by multiplying the values of three perpendicular diameters.

Equivalents

Those skilled in the art will recognize or be able to ascertain using no more than routine experimentation, many equivalents to the specific embodiments of the invention describe herein. Such equivalents are intended to be encompassed by the following claims.

We claim:

1. A method of suppressing tumor formation in a mammal comprising administering to said mammal a therapeutically affective amount of JE/Monocyte Chemoattractant Protein-1 (JE/MCP-1).

2. A method of increasing a monocyte mediated tumoricidal activity in a mammal comprising administering to said mammal an effective amount of JE/Monocyte Chemoattractant Protein-1.

3. A method of treating a localized side-effect of malignancy in a mammal comprising locally administering to the mammal a therapeutically effective amount of JE/Monocyte Chemoattractant Protein-1.

4. The method of claim 3 wherein the side effect is selected from the group consisting of pleural effusions or ascites.

5. A method of suppressing tumor formation in a mammal comprising administering to said mammal tumor killing cells which express JE/Monocyte Chemoattractant Protein-1.

6. A method of claim 5, wherein the tumor killing cells are tumor infiltrating lymphocytes.

* * * * *